United States Patent
Long et al.

(10) Patent No.: US 8,138,192 B2
(45) Date of Patent: Mar. 20, 2012

(54) INJECTABLE MECLIZINE FORMULATIONS AND METHODS

(75) Inventors: Walker Anderson Long, Chapel Hill, NC (US); Edwin Curran Murphy, III, Durham, NC (US)

(73) Assignee: Genebiology, Inc., Chapel Hill, NC (US)

( * ) Notice: Subject to any disclaimer, the term of this patent is extended or adjusted under 35 U.S.C. 154(b) by 1008 days.

(21) Appl. No.: 11/980,845

(22) Filed: Oct. 31, 2007

(65) Prior Publication Data

US 2009/0111833 A1  Apr. 30, 2009

(51) Int. Cl.
*A61K 31/495* (2006.01)
(52) U.S. Cl. .............................. 514/255.03; 514/255.04
(58) Field of Classification Search ............. 514/255.03, 514/255.04
See application file for complete search history.

(56) References Cited

U.S. PATENT DOCUMENTS

| | | | |
|---|---|---|---|
| 4,729,997 A | 3/1988 | Wenig | |
| 6,383,471 B1 | 5/2002 | Chen et al. | |
| 6,455,533 B1 | 9/2002 | Fanara et al. | |
| 6,699,505 B2 | 3/2004 | Shastri et al. | |
| 2002/0032217 A1 | 3/2002 | Fanara et al. | |
| 2006/0120967 A1 | 6/2006 | Namburi et al. | |

FOREIGN PATENT DOCUMENTS

JP  60-204712  10/1985

OTHER PUBLICATIONS

Habib et al., Canadian Journal of Anesthesia, 2004, vol. 51(4), pp. 326-341.*
Hain et al., Neurologic Clinics, 2005, vol. 23, pp. 831-853.*
Ahmed, Mahrous Osman, "Comparison of impact of the different hydrophilic carriers on the properties of piperazine-containing drug", European Journal of Pharmaceuticals and Biopharmaceutics, 2001, pp. 221-226, vol. 51.
Becirevic, M., et al., "Improvement of in vitro dissolution characteristic of meclizine hydrochloride by cyclodextrin complexation", Pharmazie, 1992, pp. 202-204, vol. 47.
Jarvinen, Tomi, et al., "β-Cyclodextrin Derivatives, SBE4-β-CD and HP-β-CD, Increase the Oral Bioavailability of Cinnarizine in Beagle Dogs", Journal of Pharmaceutical Sciences, Mar. 1995, pp. 295-299, vol. 84, No. 3.
Thompson, Diane O., "Cyclodextrins-Enabling Excipients: The Present and Future Use in Pharmaceuticals", Critial Reviews in Therapeutic Drug Carrier Systems, 1997, pp. 1-104, vol. 14, No. 1.
Saket, M.M. "Comparitive evaluation of micellar solubilization and cyclodextrin inclusion complexation for meclizine hydrochloride", Alexandria Journal of Pharmaceutical Sciences, 1996, p. 13-18, vol. 10(1).
Tong, Wei-Qin, et al. "Microcalorimetric investigation of the complexation between 2-hydroxypropyl-β-cyclodextrin and amine drugs with the diphenylmethyl functionality", Journal of Pharmaceuticals and Biomedical Analysis, 1991, pp. 1139-1146, vol. 9, No. 10-12.
Tong, Wei-Qin, et al., "Structural Effects on the Binding of Amine Drugs with the Diphenylmethyl Functionality to Cyclodextrins. I. A Microcalorimetric Study", Pharmaceutical Research, 1991, pp. 951-957, vol. 8, No. 7.
Tong, Wei-Qin, et al. "Structural Effects on the Binding of Amine Drugs with the Diphenylmethyl Functionality to Cyclodextrins. II A Molecular Modeling Study", Pharmaceuticals Research, 1991, pp. 1307-1312, vol. 8, No. 10.
International Search Report, corresponding to International Patent Application No. PCT/US2008/081973, dated Jun. 25, 2009.
Written Opinion, corresponding to International Patent Application No. PCT/US2008/081973, dated Jun. 25, 2009.
Chovan, J.P. et al. "Comparison of meclizine levels in the plasma of rats and dogs after intranasal, intravenous, and oral administration." Journal of Pharmaceutical Sciences. 1985, 74(10), 1111-1113.
Challa, R. et al. "Cyclodextrins in drug delivery: an updated review." AAPS PharmSciTech. 2005, 6(2), E329-E357.
Stella, V.J. et al. "Cyclodextrins: Their future in drug formulation and delivery." Pharmaceutical Research. 1997, 14 (5), 567-567.
Strickley, R.G. "Solubilizing expients in oral and injectable formulations." Pharmaceutical Research. 2004, 21(2). 201-230.
Cohen, Bernard, et al., "Meclizine and Placebo in Treating Vertigo of Vestibular Origin—Relative Efficacy in Double-Blind Study", Arch Neurol 27:129-135 (1972).
New Zealand Intellectual Property Office, Examination Report for Patent Application No. 584942 dated Feb. 3, 2011.
Hirayama, Fumitoshi et al., Improving the Aqueous Stability of Prostaglandin E2 and Prostaglandin A2 by Inclusion Complexation with Methylated-β-Cyclodextrins, Chem. Pharm. Bull., 1984, pp. 4237-4240, vol. 32, issue 10.

* cited by examiner

*Primary Examiner* — James D Anderson
(74) *Attorney, Agent, or Firm* — Christopher J. Knors; Moore & Van Allen PLLC

(57) ABSTRACT

Methods of treating or preventing a vertigo, nausea, or vomiting condition comprising injecting a subject with a pharmaceutically acceptable formulation consisting essentially of an effective amount of meclizine or a pharmaceutically acceptable salt thereof, a chemically modified cyclodextrin, and an aqueous carrier medium having a pH between about 2 and about 7 are disclosed. An injectable pharmaceutical formulation for treating or preventing a vertigo, nausea, or vomiting condition consisting essentially of an effective amount of meclizine, a chemically modified cyclodextrin, and an aqueous carrier medium having a pH between about 2 and about 7 is also disclosed.

33 Claims, 5 Drawing Sheets

INJECTABLE MECLIZINE FORMULATIONS AND METHODS

BACKGROUND

Field

This invention relates to methods of treating vertigo conditions by administration of an injectable pharmaceutical formulation comprising meclizine and a chemically modified cyclodextrin. This invention further relates to methods of treating nausea or vomiting conditions by administration of an injectable pharmaceutical formulation comprising meclizine and a chemically modified cyclodextrin.

Vertigo is a disabling disorder. The most common cause of vertigo is benign paroxysmal positional vertigo (BPPV). Vertigo may be a symptom of an underlying cause, such as in BPPV, or it may be suggestive of a more serious problem such as drug toxicities (e.g., gentamicin), strokes or tumors. Vertigo may be comorbid with skull fractures or brain trauma, sudden changes of blood pressure, or as a symptom of motion sickness. Vertigo may cause or include extreme dizziness, nausea, or vomiting episodes.

Nausea is a sensation of unease and discomfort in the stomach, usually accompanied by an urge to vomit. Nausea is medically not an illness; it is a symptom of several conditions, many of which may not be related to the stomach. Nausea may be indicative of an underlying condition elsewhere in the body. Motion sickness, which is due to confusion between perceived and actual movement, is an example. Nausea may result as an adverse effect of a drug. Nausea may be a problem during some chemotherapy regimens and following general anesthesia.

There are several types of anti-emetics, however, many pharmacological treatments, which are effective for nausea and vomiting in some medical conditions, may not be effective for other medical conditions. For example, metoclopramide and prochlorperazine, although widely used as anti-emetics, are ineffective for motion-sickness prevention and treatment.

Once vomiting has commenced, oral anti-emetic treatments become substantially ineffective. This may be because the orally administered drug may not be retained for a sufficient period of time to allow absorption from the stomach. Oral anti-emetic drugs may require up to 45-90 minutes for achieving their clinical effect and are thus not effective in treating expected vomiting episodes. In order for oral treatment regimes to be effective, the regimes would necessarily need to be ingested 1-2 hours prior to the expected vomiting episode. The net result is longer ER visits and often hospital admissions for patients with nausea-related conditions. Moreover, this limitation of oral anti-emetics makes them unsuitable for administration to post-anesthetized or unconscious subjects.

Intravenous anti-emetics are few in number, for example, cyclizine, may currently offer an alternative to oral anti-emetic therapies for the treatment and prevention of nausea and vomiting, however, it presents with a very short duration of action (1-2 hours). Such short duration of action limits the clinical application of cyclizine.

Meclizine is commercially available as an oral and as a chewable tablet. It is used in the treatment and prevention of nausea and vertigo associated with Mèniére's syndrome and in the treatment and prevention of motion sickness. It has also been used for the symptomatic treatment relief of hypersensitivity reactions and in pruritic skin disorders. See *Martindale* 30, 941. It is usually given in divided daily doses of 25-50 mg, with divided daily doses of up to 100 mg being used to treat severe vertigo and labyrinth disorders. Both meclizine base and meclizine HCl have been administered by the rectal route in similar doses to those administered by mouth. There are, however, no marketed meclizine rectal preparations. See *Martindale* 30, 941. There are also currently no marketed hypodermically administrable meclizine HCl formulations available. This may be attributed primarily to the poor aqueous solubility of meclizine HCl. Meclizine is virtually water insoluble, with meclizine HCl presenting with a water solubility of 0.1 g/100 ml. *Merck Index*, 12th Ed, 984. In particular, meclizine exhibits very low solubility at pH values greater than 2.0. Such pH values are desirable for reasons of injection comfort. Meclizine's anti-emetic duration of action may last up to 24 hours.

Thus, there is a need to provide stable, non-colloidal, injectable anti-emetic therapeutic formulations with longer duration of action, such as 12-24 hours. There is a need to provide otherwise insoluble and/or unstable anti-emetics, such as meclizine, as injectable therapeutic formulations for the treatment and prevention of nausea and vertigo. There is also a need to provide a viable hypodermic formulation for the treatment of nausea and vomiting as a clinically effective alternative to oral dosage forms.

SUMMARY

In an embodiment, a method of treating a vertigo condition in a subject in need thereof is provided. The method comprises injecting the subject with a pharmaceutically acceptable formulation consisting essentially of a therapeutically effective amount of meclizine, a chemically modified cyclodextrin, where the molar ratio of the meclizine to the chemically modified cyclodextrin is 1:>1, and an aqueous carrier medium having a pH between about 2 to about 7. Optionally, a pharmaceutically acceptable preservative, a pharmaceutically acceptable antioxidant, a pharmaceutically acceptable osmolality adjusting agent, or mixtures thereof, may be added.

In another embodiment, an injectable pharmaceutical formulation for treating a vertigo condition of a subject is provided. The injectable pharmaceutical formulation consists essentially of a therapeutically effective amount of meclizine, a molar excess of 2-hydroxypropyl-β-cyclodextrin, and an aqueous carrier medium. The aqueous carrier medium has a pH between about 2 to about 7. Optionally, a pharmaceutically acceptable preservative, a pharmaceutically acceptable antioxidant, a pharmaceutically acceptable osmolality adjusting agent, or combination thereof, may be added.

In another embodiment, an injectable pharmaceutical formulation for treating and/or preventing a vertigo, nausea, or vomiting condition in a subject in need thereof is prepared by the steps of providing a chemically modified cyclodextrin solution in a pharmaceutically acceptable aqueous carrier medium, combining a therapeutically effective amount of meclizine with the chemically modified cyclodextrin solution, and adjusting the pharmaceutically acceptable aqueous carrier medium pH to between about 2 to about 7. The molar ratio of the meclizine to the chemically modified cyclodextrin solution is 1:>1. Optionally, a pharmaceutically acceptable preservative, a pharmaceutically acceptable antioxidant, a pharmaceutically acceptable osmolality adjusting agent, or combination thereof, may be added.

In another embodiment, a method of treating or preventing a nausea or vomiting condition in a subject in need thereof is provided. The method comprises injecting a subject with a pharmaceutically acceptable formulation consisting essentially of a therapeutically effective amount of meclizine, a chemically modified cyclodextrin, where the molar ratio of the meclizine to the chemically modified cyclodextrin is 1:>1, and an aqueous carrier medium having a pH between about 2 to about 7. Optionally, a pharmaceutically acceptable preservative, a pharmaceutically acceptable antioxidant, a pharmaceutically acceptable osmolality adjusting agent, or mixtures thereof may be added.

In another embodiment, an injectable pharmaceutical formulation for treating or preventing a nausea or vomiting condition is provided. The injectable pharmaceutical formulation consists essentially of a therapeutically effective amount of meclizine, a molar excess of 2-hydroxypropyl-β-cyclodextrin, and an aqueous carrier medium. The aqueous carrier medium has a pH between about 2 to about 7. Optionally, a pharmaceutically acceptable preservative, a pharmaceutically acceptable antioxidant, a pharmaceutically acceptable osmolality adjusting agent, or combination thereof, may be added.

DETAILED DESCRIPTION

Figure 1:
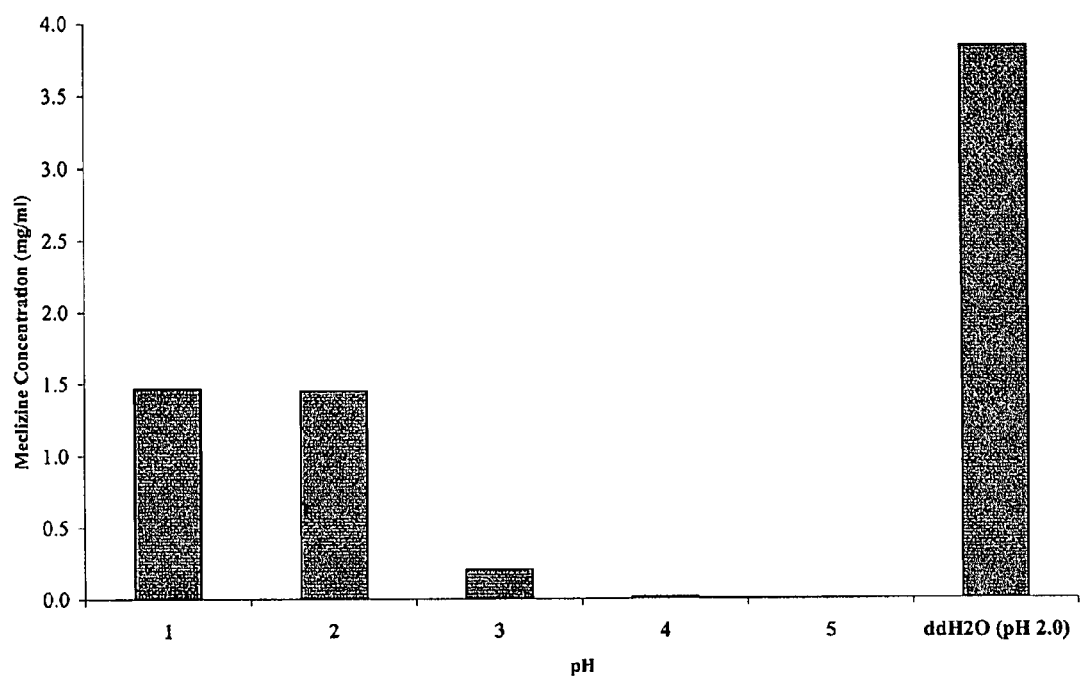
FIG. 1 depicts graphically the effect of pH (0.1 M citric acid buffer) on the aqueous solubility of meclizine.

An injectable pharmaceutical formulation consisting essentially of meclizine and a chemically modified cyclodextrin is described. Formulations according to the invention are stable, non-colloidal aqueous solutions containing up to 100 mg/ml meclizine for hypodermic administration.

The meclizine/cyclodextrin pharmaceutical formulations are suitable for administration to a subject in need thereof of treatment of a vertigo, nausea, or vomiting condition. The meclizine/cyclodextrin formulations provides for methods of treating or preventing a vertigo, nausea, or vomiting condition or related complication. The meclizine/cyclodextrin formulations also provides for administration of a hypodermically effective amount of a meclizine/cyclodextrin formulation to an unconscious or post-anesthesized subject treating or preventing a vertigo, nausea, or vomiting condition. Preparation of meclizine/cyclodextrin formulations suitable for direct or reconstitutable hypodermic administration is also provided. Compositions consisting of stable non-colloidal aqueous solutions contain up to 100 mg/ml of meclizine suitable for hypodermic administration are described.

Prior to describing the methods herein disclosed in further detail, however, the following terms will first be defined.

DEFINITIONS

The terms "meclizine" or "meclozine" are used interchangeably and refer to the compound having the chemical name 1-(4-chlorobenzhydryl)-4-(3-methylbenzyl)-piperazine. The term "meclizine" includes, meclizine base, its pharmaceutically acceptable salts, for example, meclizine•2HCl 1-(4-chlorobenzhydryl)-4-(3-methylbenzyl)-piperazine dihydrochloride, or its hydrates. Other pharmaceutically acceptable salts of meclizine base may be used. Meclizine•2HCl monohydrate is generally preferred.

As used herein, the phrase "nausea or vomiting condition" refers to symptoms normally associated with nausea or emesis. The phrase "nausea or vomiting condition" includes nausea- or vomiting-related disorders.

As used herein, the phrase "vertigo condition" refers to symptoms normally associated with vertigo. The phrase "vertigo condition" includes vertigo-related disorders.

As used herein, the term "prevent" and its grammatical equivalents refer to any reduction of a subject's predisposition or risk for developing a nausea or vomiting condition. The term "prevent" includes either preventing a clinically evident nausea or vomiting condition from occurring altogether or preventing a pre-clinically evident nausea or vomiting condition in an individual at risk for such a condition from occurring. For example, the term "prevent" includes any reduction of a subject's predisposition or risk for developing a nausea or vomiting condition as a result of chemotherapy regimens and/or pre-, peri-, or post-anesthesia.

As used herein, the term "treatment" and its grammatical equivalents refer to the alleviation or elimination of symptoms and include, for example, the elimination of such symptom causation either on a temporary or permanent basis, or to alter or slow the appearance of such symptoms or symptom worsening. For example, the term "treatment" includes alleviation or elimination of causation of symptoms associated with, but not limited to, vertigo, nausea, vomiting, or any vertigo, nausea, or vomiting related-complications described herein.

"Therapeutically effective" as used herein, refers qualitatively to the amount of meclizine that will achieve the goal of preventing or improving in the severity of, the nausea, vomiting, or vertigo condition being treated. A vertigo, nausea, or vomiting condition symptom or its related complication is considered ameliorated or improved if any benefit is achieved, irrespective of the absolute magnitude of the amelioration or improvement. For example, any reduction in nausea of a subject suffering from a nausea condition, such as post-anesthetic nausea, would be considered an ameliorated symptom. Likewise, any inhibition or suppression of vomiting would also be considered amelioration of a vomiting condition. Furthermore, any reduction in symptom severity of a vertigo condition or its related complication is considered an ameliorated symptom of a vertigo condition.

As used herein, "therapeutically effective amount" refers to an amount of meclizine that is nontoxic but sufficient in preventing or ameliorating the severity of the nausea-, vomiting-, or vertigo-related condition being treated. For example, a therapeutically effective amount of meclizine is an amount sufficient to measurably decrease the symptom or etiology of a nausea condition. The therapeutically effective amount varies according to the patient's sex, age and weight, the route of administration, the nature of the condition and any treatments that may be associated therewith, or any concurrent related or unrelated treatments or conditions of the patient. Therapeutically effective amounts can be determined without undue experimentation by any person of ordinary skill in the art or by following the exemplary guidelines set forth in this application.

As used herein, the term "subject" for purposes of treatment includes any subject, and preferably is a subject who is in need of treatment of a vertigo, nausea, or vomiting condition. For purposes of prevention, the subject is any subject, and preferably is a subject that is at risk for, or is predisposed to, developing a vertigo, nausea, or vomiting condition. The subject is typically an animal, more typically is a mammal. Preferably, the mammal is a human.

The subject may be a human subject who is at risk for developing or is experiencing a vertigo, nausea, or vomiting condition. The subject may be at risk or experiencing such a condition due to genetic predisposition, diet, age, post-exposure to an anesthetic, head trauma, exposure to a potentially traumatic environment, exposure to nausea- or vomiting-causing agents or environment, and the like. The subject may also be at risk or experiencing such a condition due to physiological factors such as anatomical and/or biochemical abnormalities.

As used herein, "subject in need thereof" refers to any subject who is suffering from or is predisposed to a vertigo, nausea, or vomiting condition.

The terms "hypodermic," and "injection," and their grammatical equivalents are used interchangeably and refer to any delivery method suitably adapted for administering a solution to a subject. For example, "hypodermic" includes delivery methods comprising the use of a syringe, microneedle, or needleless device.

The term "injectable pharmaceutical formulation" refers generally to a pharmaceutical formulation comprising a therapeutically effective amount of a meclizine such that the pharmaceutical formulation is suitable for injection into a subject. For example, an "injectable pharmaceutical formulation" of a meclizine inclusion complex with a cyclodextrin comprises a therapeutically effective amount of meclizine and is suitable for injection into a subject. Preferably, the "injectable pharmaceutical formulation" is a clear, non-colloidal solution of a meclizine, or its inclusion complex, with a cyclodextrin.

The term "chemically modified cyclodextrin" refers to one or more chemically modified cyclodextrins where there is independently more than one degree of substitution that may vary from about 0.5 to about 10.0. The degree of substitution (the mean number of functional groups per glucose unit) of the chemically modified cyclodextrin may vary as need to provide the necessary solubility and stability of the meclizine. For example, the degree of substitution may be between from about 0.5 to about 10.0. For a chemically modified cyclodextrin such as 2-hydroxypropyl-β-cyclodextrin, the degree of substitution (of substituted hydroxy functional groups per glucose unit) may be between 3.9 and 5.1, for example. Degree of substitution may be determined by mass spectrometry (MS) or nuclear magnetic resonance (NMR) spectroscopy using known techniques.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed subject matter. For example, specified materials or steps that do not materially affect the basic and novel characteristics of the claimed subject matter would include compounds or compositions of matter present at a level which do not directly attribute to or are capable of treating or preventing a vertigo, nausea, or vomiting condition in a subject.

Cyclodextrins

Cyclodextrins suitable for use in the compositions, formulations, and methods herein disclosed are generally cyclic oligosaccharides with a cone-like shape. The interior of the cone acts as a hydrophobic cavity, while the exterior of the cone is hydrophilic. The former property enables cyclodextrins to form inclusion complexes with a wide variety of lipophilic molecules or portions thereof, which "fit" into the cavity while the latter property facilitates aqueous solubility. Cyclodextrin derivatives have been extensively studied for use as parenteral drug carriers owing to their high water solubility and low toxicity. *Cyclodextrins in Pharmacy*. Fromming, KH & Szejtli, J. 1994. Kluwer Academic Publishers, pp 1-44. Clinical studies on healthy volunteers showed, for example, that an intravenous infusion of Encapsin-HPB© (parenteral grade 2-hydroxypropyl-β-cyclodextrin, Janssen Pharmaceutica) at a dose of 3 g, given as a single dose, was safe and well tolerated. Junge et al., *Janssen Clinical Research Report*, July 1988.

Chemically Modified Cyclodextrins

The cyclodextrin suitable for use in the compositions, formulations, and methods herein disclosed preferably are chemically modified cyclodextrins. The chemically modified cyclodextrins may include derivatives of α-cyclodextrin, β-cyclodextrin, or γ-cyclodextrin. The chemically modified cyclodextrins may include, but are not limited to methyl-β-cyclodextrin, 2-6-di-O-methyl-β-cyclodextrin, randomly methylated-β-cyclodextrin, ethyl-β-cyclodextrin, carboxymethyl-β-cyclodextrin, diethylaminoethyl-β-cyclodextrin, 2-hydroxypropyl-β-cyclodextrin, 3-hydroxypropyl-β-cyclodextrin, 2,3-dihydroxypropyl-β-cyclodextrin, and sulfobutyl ether-β-cyclodextrin. Preferably, the chemically modified cyclodextrin is 2-hydroxypropyl-β-cyclodextrin, 3-hydroxypropyl-β-cyclodextrin, 2,3-dihydroxypropyl-β-cyclodextrin, and sulfobutyl ether-β-cyclodextrin. More preferably, the chemically modified cyclodextrin is 2-hydroxypropyl-β-cyclodextrin or sulfobutyl ether-β-cyclodextrin. Preferably, the degree of substitution for 2-hydroxypropyl-β-cyclodextrin is between 3.9 and 5.1.

Preparation of Pharmaceutical Formulations

According to a first aspect of the invention, there is provided a method of preparing a pharmaceutical formulation for administration as an injection comprising an inclusion complex of meclizine and a chemically modified cyclodextrin with a stoichiometry of 1:>1 mol/mol. Preferably, the cyclodextrin degree of substitution is 0.5-10.0.

According to a second aspect of the invention, there is provided a method of preparing a pharmaceutical formulation for administration as an injection comprising a solid inclusion complex of meclizine and a chemically modified cyclodextrin with a stoichiometry of 1:>1 mol/mol. Preferably, the cyclodextrin degree of substitution is 0.5-10.0.

For example, an inclusion complex is formed between meclizine HCl and a chemically modified cyclodextrin, such as 2-hydroxypropyl-β-cyclodextrin (HPBCD), sulfobutyl ether-β-cyclodextrin (SEBCD), or randomly methylated-β-cyclodextrin (RAMEB) and wherein the molar stoichiometry of meclizine to chemically modified cyclodextrin is 1:>1.

According to a third aspect of the invention, there is provided a method of preparing a pharmaceutical formulation for hypodermic administration comprising an inclusion complex of meclizine and a chemically modified cyclodextrin with a stoichiometry of 1:>1 mol/mol, which may optionally include a pharmaceutically acceptable anti-oxidant such as acetylcysteine, EDTA, sodium metabisulphite, monothioglycerol, or potassium nitrate; a pharmaceutically acceptable preservative such as benzalkonium chloride, bronopol, chlorhexidine gluconate, chlorobutanol, or benzyl alcohol; a pharmaceutically acceptable osmolality adjusting agent, such as glycerol, dextrose, mannitol, or sorbitol; or mixtures thereof.

The preparation of pharmaceutical formulations as herein disclosed involves dissolving the chemically modified cyclodextrin in a suitable volume of aqueous carrier medium (for example, water for injection), removal of oxygen (for example, with nitrogen, inert gas, or freeze-thaw under vacuum), followed by the gradual addition of meclizine to the cyclodextrin solution under vigorous stirring until essentially all of the meclizine has been complexed and is in solution. The temperature of the cyclodextrin solution may be between 0-80° C. Preferably the temperature of the cyclodextrin solution is maintained between about 20-60° C.

After addition of the meclizine, the solution may be brought to a final volume with de-oxygenated aqueous carrier medium. The solution may then be sterilized, for example, by filtration and/or aseptically transferred to vials or ampoules. The solution may be transferred directly to ampoules for sterilization by autoclaving or irradiation. The vials or ampoules may be sealed under an inert gas, such as nitrogen. The molar ratio of meclizine to chemically modified cyclodextrin is 1:>1 mol/mol. Preferably, the molar ratio of meclizine to chemically modified cyclodextrin is about 1:2 to about 1:30. More preferably, the molar ratio of meclizine to chemically modified cyclodextrin is about 1:13 mol/mol.

Pharmaceutical Formulations

The composition containing an inclusion complex of meclizine and a chemically modified cyclodextrin with a stoichiometry of 1:>1 mol/mol and may be formulated as pharmaceutical formulation suitable for injection. The pharmaceutical formulation may contain a concentration of meclizine of 0.05 to 100 mg/ml, preferably 0.25 to 50 mg/ml, more preferably 0.1 to 10 mg/ml, or even more preferably about 5 mg/ml. The composition may be diluted further with suitable diluents, such as water for injection (WFI), aqueous dextrose solution, or aqueous sodium chloride solution.

The pharmaceutical formulation may have a final pH of 1.0 to 10.0, preferably a pH of 2 to 7, or more preferably a pH of 3.0-5.0. The pH may be adjusted by methods commonly used in the art, for example, with HCl to reduce the pH or with NaOH to increase the pH. Other acids or bases may be used.

The pharmaceutical formulation may optionally contain a pharmaceutically acceptable antioxidant such as acetylcysteine, edetate disodium (EDTA), sodium metabisulphite, monothioglycerol, potassium nitrate, or mixtures thereof, and a pharmaceutically acceptable preservative such as benzalkonium chloride, bronopol, chlorhexidine gluconate, chlorobutanol, benzyl alcohol, or mixtures thereof, and a pharmaceutically acceptable osmolality adjusting agent such as glycerol, dextrose, mannitol, sorbitol, or mixtures thereof.

The pharmaceutical formulation may be formulated as a solution for injection, a freeze-dried powder suitable for reconstitution for injection, a suspension for injection, or an emulsion for injection. For example, the pharmaceutical formulations may be freeze-dried or lyophilized to form a solid inclusion complex of meclizine and a chemically modified cyclodextrin suitable for reconstitution and injection. The freeze-dried or lyophilized solid inclusion complex for injection may be reconstituted prior to administration with a suitable volume of water for injection, aqueous dextrose, aqueous sodium chloride, or any other suitable diluent. The reconstituted freeze-dried or lyophilized solid inclusion complex for injection preferably provides a clear, particle free solution suitable for any hypodermic administration such as, for example, intramuscularly, intravenously, subcutaneously, or intradermally.

During the preparation of the solid inclusion complex, the meclizine-chemically modified cyclodextrin solution may be sterilized by filtration, whereafter it may be freeze-dried in a sterile environment and sealed under an inert gas such as nitrogen.

The pharmaceutical formulation may be delivered by syringe, microneedle, or needleless device. The pharmaceutical formulation may be formulated in conventional ampoules, vials, univials (vials containing two separate compartments in a single vial), or pre-filled syringes or other devices.

Without being held to any theory, it is believed that the excess chemically modified cyclodextrin present in the pharmaceutical formulation acts to stabilize the meclizine inclusion complex.

Methods of Treating or Preventing Nausea, Vomiting, or Vertigo

The pharmaceutical formulations as described above may be used in the treatment and prevention of nausea, vomiting and vertigo conditions, for example, conditions associated with Meniere's syndrome, nausea and vertigo following anesthesia or in the treatment and prevention of motion sickness.

A subject in need thereof of treatment or prevention of nausea, vomiting, or vertigo, is administered a therapeutically effective amount of an injectable formulation consisting essentially of a meclizine inclusion complex with a chemically modified cyclodextrin in an aqueous carrier medium. Administration of the formulation may be from 0 up to 24 hours, from 0 up to 12 hours, from 0 up to 6 hours, or from 0 up to 4 hours before the expected nausea or vomiting episode for the preventative treatment of postoperative nausea and vomiting. The expected nausea or vomiting episode may result from chemotherapy administration or 0-24 hours prior to patient recovery, following anesthesia. The formulation may optionally include a pharmaceutically acceptable antioxidant, a pharmaceutically acceptable preservative, a pharmaceutically acceptable osmolality adjusting agent, or mixtures thereof. The meclizine concentration is between 0.05 to 100 mg/ml, preferably 0.25 to 50 mg/ml, more preferably 0.1 to 10 mg/ml, or even more preferably about 5 mg/ml. The chemically modified cyclodextrin is preferably HPBCD and the HPBCD preferably has a degree of substitution of between about 3.9 to about 5.1. The aqueous carrier medium preferably has a pH of between about 2 and about 7. The molar ratio of meclizine to HPBCD is preferably 1:>1.

The following examples are illustrative and not to be interpreted as limiting or restrictive. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. For example, the use of the term "about" in reference to a numerical value refers to a range of approximately ±10 percent unless specified otherwise. In the following examples, meclizine dihydrochloride monohydrate was used.

EXAMPLE 1

Citric acid (0.1M) buffer solutions are prepared with pH's of 1.0; 2.0; 3.0; 4.0, and 5.0 in ddH$_2$O (de-oxygenated water by purging with nitrogen gas). 2 ml of each buffer are placed in 4 ml vials and 2 ml ddH$_2$O is placed in a 4 ml vial. 20 mg meclizine HCl is added to each vial. The vials are sealed and are shaken on an orbital shaker for 24 hours at 200 rpm. Following the shaking, the vial contents are filtered through 0.45 μm filters to remove any excess solute. The remaining solution is assayed by HPLC for meclizine content. As shown in FIG. 1, the aqueous solubility of meclizine decreases with an increase in pH from about 1.5 mg/ml at pH 1.0 to below the limit of detection at about pH 5.0. The aqueous solubility of meclizine in ddH$_2$O is found to be about 3.8 mg/ml and has a measured pH of about 2.0.

EXAMPLE 2

Figure 1A:
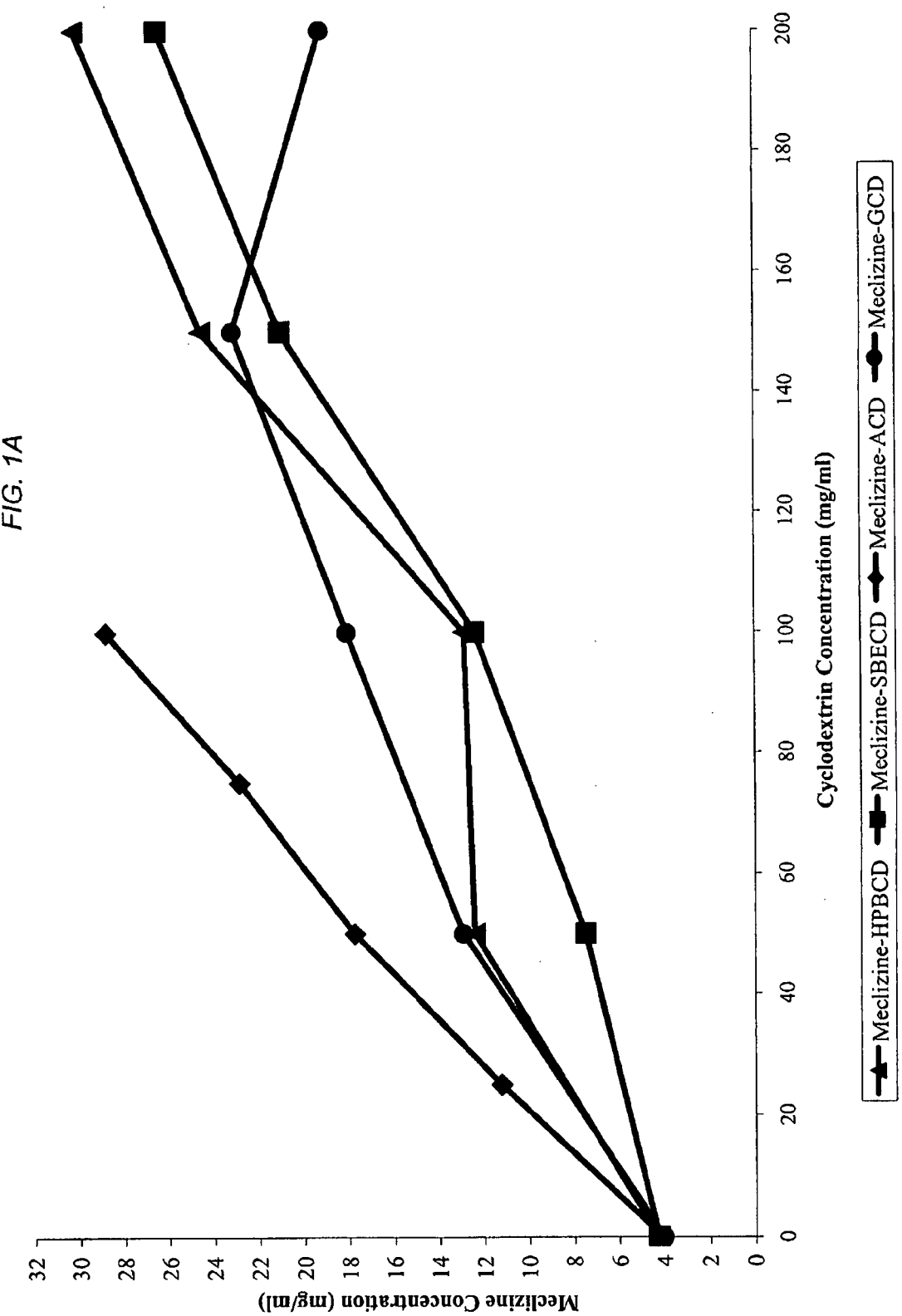
FIG. 1A depicts graphically the relationship of meclizine concentration with increasing cyclodextrin concentration in $ddH_2O$.

FIG. 1A depicts solubility data of meclizine complexed with non-chemically modified cyclodextrins (α-CD at 0-100 mg/ml, γ-CD at 200 mg/ml), chemically modified cyclodextrins (HPBCD and SBECD) at 200 mg/ml, and with no CD complexation in ddH$_2$O. Solutions were prepared by adding excess meclizine to ddH$_2$O samples with varying quantities of the different cyclodextrins. These samples were shaken for 24 hours at 200 rpm. Following the shaking, the vial contents were filtered through 0.45 μm filters to remove any excess solute. The remaining solution was assayed by HPLC for meclizine content. The data of FIG. 1A shows improved solubility of meclizine with all of the cyclodextrin used and demonstrates that the aqueous solubility of meclizine is enhanced in the presence of cyclodextrins.

EXAMPLE 3

Figure 2:
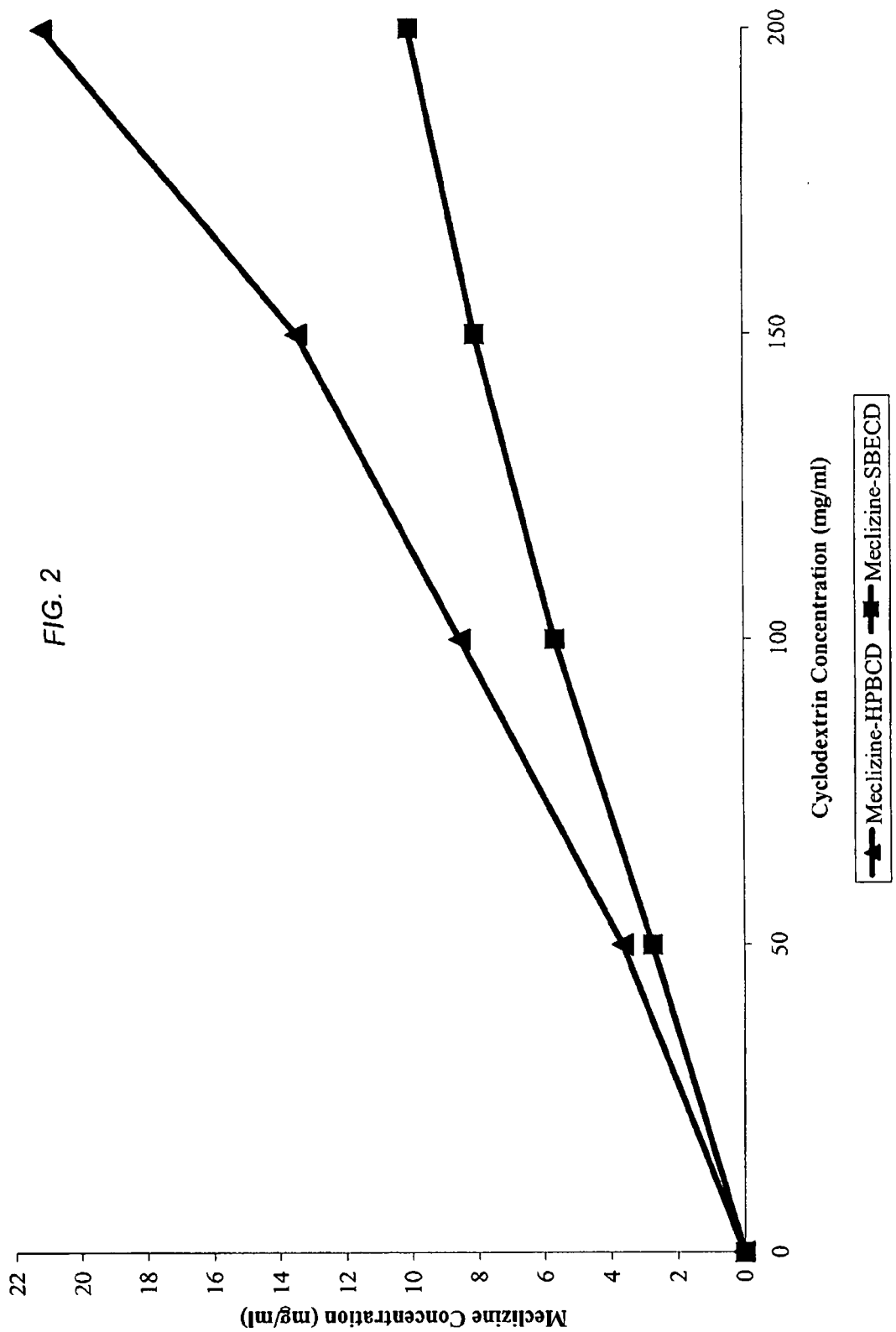
FIG. 2 depicts graphically the effect of increasing concentrations of 2-hydroxypropyl-β-cyclodextrin (HPBCD) and sulfobutyl ether-β-cyclodextrin (SBECD) on the aqueous solubility of meclizine in 0.5 M citric acid buffer at pH 3.0.

Five HPBCD and five SBECD solutions in 0.5 M citric acid buffer (pH of 3.0) are prepared, with HPBCD and SBECD concentrations of 50; 100; 150 and 200 mg/ml. 3 ml of the various buffered HPBCD and SBECD solutions are placed in 4 ml vials. 75-100 mg meclizine is added to each vial, such that excess meclizine is provided. The vials are sealed and are shaken on an orbital shaker for 24 hours at 200 rpm and 25° C. Following the shaking, the vials are filtered through 0.45 μm filters to remove any excess solute. The remaining solution is assayed by HPLC for meclizine content. As shown in FIG. 2, the aqueous solubility of meclizine at pH 3.0 increases from about 0.30 mg/ml (with no HPBCD or SBECD) in a linear fashion to about 20 mg/ml at an HPBCD concentration of 200 mg/ml and 7.10 mg/ml at a SBECD concentration of 200 mg/ml. Thus, the meclizine aqueous solubility is enhanced with an increase in chemically modified cyclodextrin concentration.

Figure 2A:
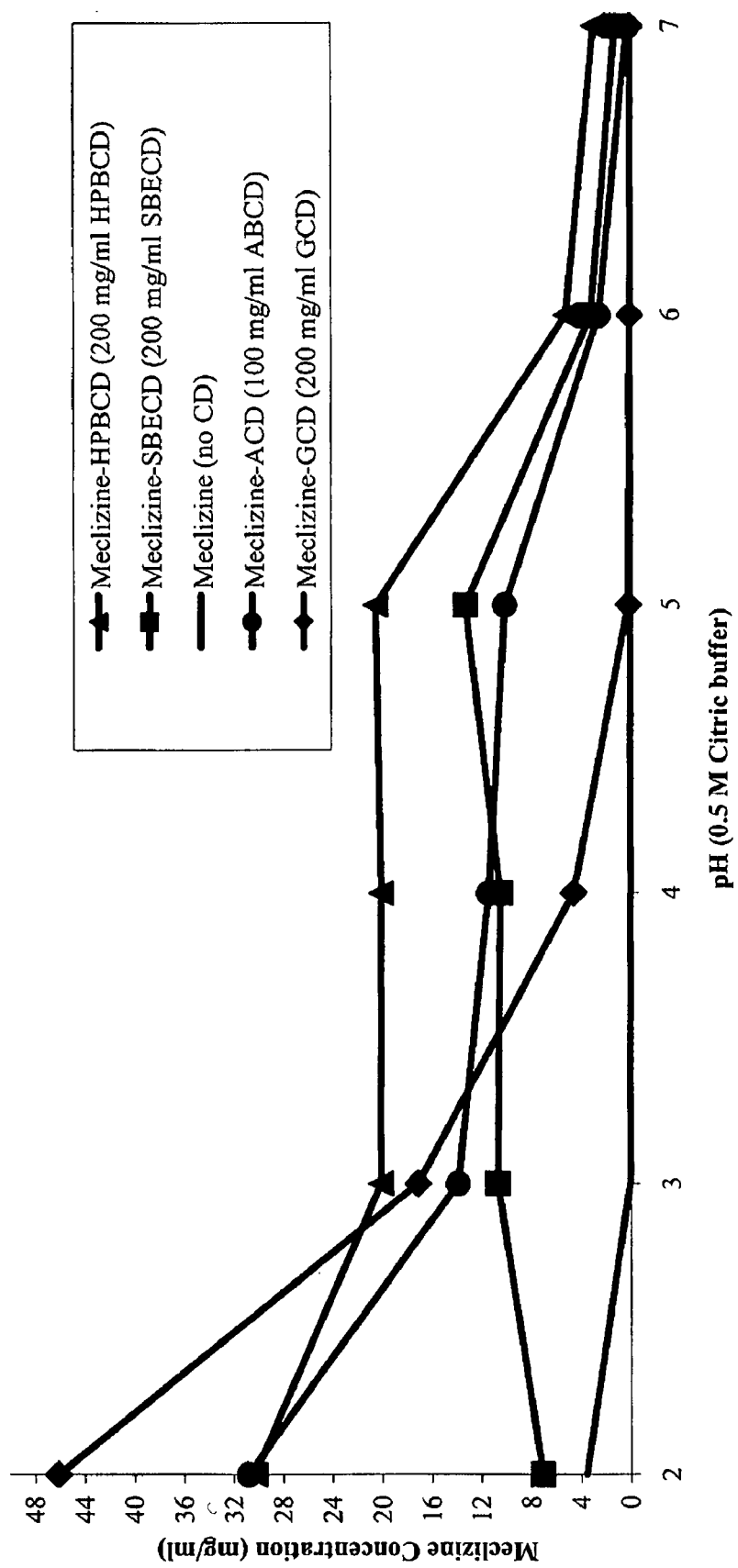
FIG. 2A depicts graphically the pH-dependent solubility of meclizine cyclodextrin complexes in 0.5 M citric acid buffer.

FIG. 2A depicts the solubility of meclizine in non-chemically modified cyclodextrins (α-CD at 0-100 mg/ml, γ-CD at 200 mg/ml) with HPBCD and SBECD at 200 mg/ml compared with no CD in 0.5 M citric buffer. The data shows improved solubility of meclizine in HPBCD at higher pH, especially above pH of about 5 compared with the non-chemically modified CD's. While the non-chemically modified ACD enhances the solubility of meclizine to a similar extent as that seen for HPBCD and at a lower cyclodextrin concentration (100 mg/ml ACD), toxicological concerns of these quantities of ACD may not be viable for a parenteral formulation.

EXAMPLE 4

Figure 3:
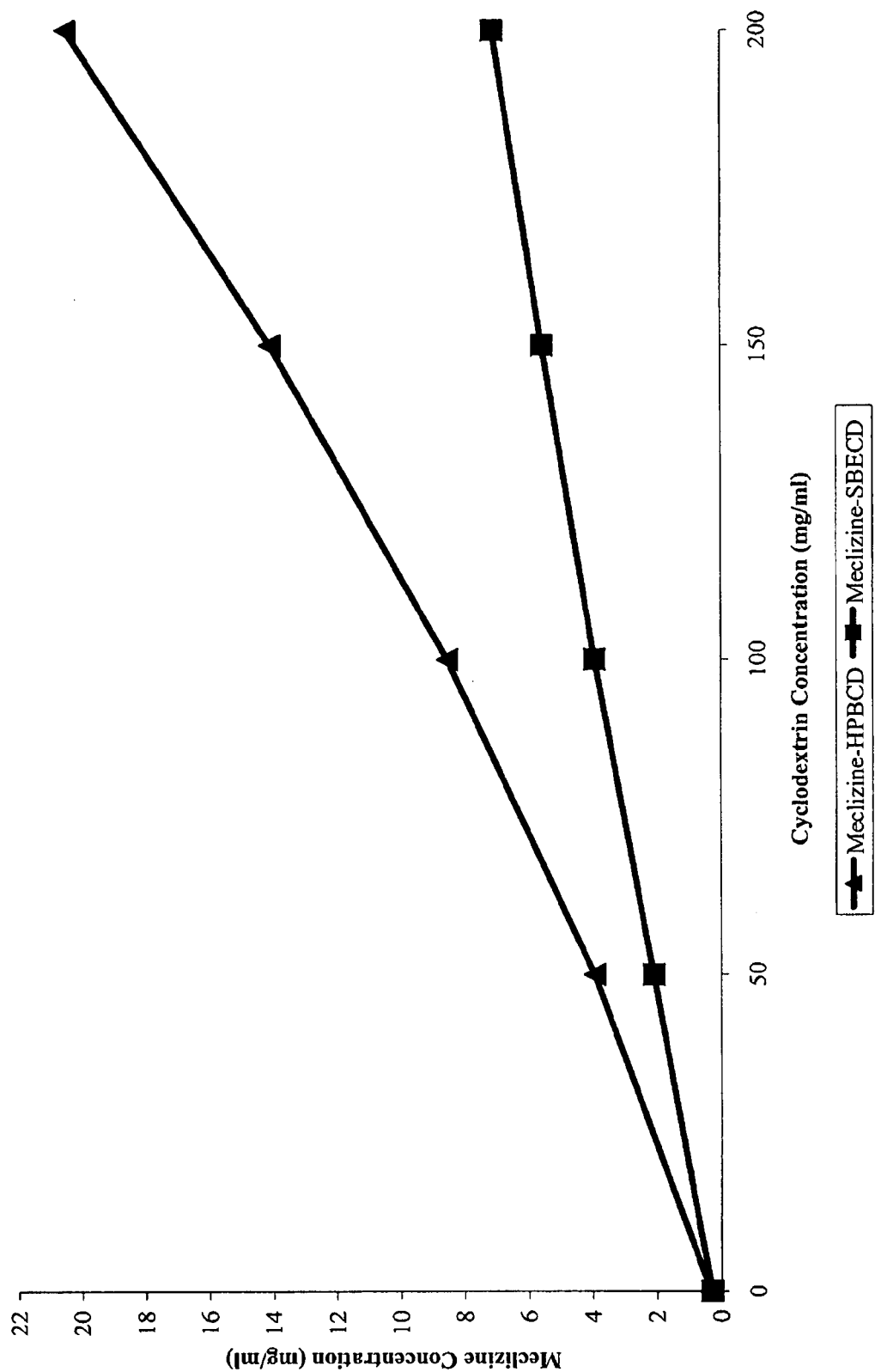
FIG. 3 depicts graphically the effect of increasing concentrations of 2-hydroxypropyl-β-cyclodextrin (HPBCD) and sulfobutyl ether-β-cyclodextrin (SBECD) on the aqueous solubility of meclizine in 0.5 M citric acid buffer at pH 4.0.

Five HPBCD and five SBECD solutions in 0.5 M citric acid buffer (pH of 4.0) are prepared, with HPBCD and SBECD concentrations of 0; 50; 100; 150 and 200 mg/ml. 3 ml of the various buffered HPBCD and SBECD solutions are placed in 4 ml vials. 50-100 mg meclizine is added to each vial, such that excess meclizine is available. The vials are sealed and are shaken on an orbital shaker for 24 hours at 200 rpm and 25° C. Following the shaking, the vials are filtered through 0.45 μm filters to remove any excess solute. The remaining solution is assayed by HPLC for meclizine content. As shown in FIG. 3, the aqueous solubility of meclizine at pH 4.0 increases from about 0.01 mg/ml (with no HPBCD or SBECD) in a linear fashion to about 21 mg/ml at an HPBCD concentration of 200 mg/ml and 10 mg/ml at an SBECD concentration of 200 mg/ml. Thus, the meclizine aqueous solubility is enhanced with an increase in chemically modified cyclodextrin concentration at higher pH.

EXAMPLE 5

2000 mg HPBCD is weighed off and dissolved in 25 ml ddH$_2$O at ambient temperature. The volume is brought to 35 ml with ddH$_2$O. 200 mg meclizine is added to the HPBCD solution and is vigorously stirred for 60 minutes, during which time essentially all of the meclizine is complexed and goes into solution. The pH is measured to be 2.1 and is adjusted to 3.5 with a 0.5 M NaOH solution. The meclizine-HPBCD solution is made to 40 ml volume with de-oxygenated ddH$_2$O. The meclizine-HPBCD solution is sterile filtered through 0.22 μm filters and filled aseptically into 1 ml vials. The meclizine content and stability was determined and monitored by HPLC on a monthly basis. HPLC analysis demonstrated that the meclizine-HPBCD solution was stable at 25° C. and at 40° C. for at least 6 months.

EXAMPLE 6

2000 mg HPBCD is weighed off and dissolved in 25 ml ddH$_2$O at ambient temperature. The volume is brought to 35 ml with ddH$_2$O. 200 mg monothioglycerol is added to the solution. 200 mg meclizine is added to the HPBCD and monothioglycerol solution and is vigorously stirred, during which time essentially all of the meclizine is complexed and goes into solution. The pH is measured to be 2.1 and is adjusted to 3.5 with a 0.5 M NaOH solution. The meclizine-HPBCD solution is made to 40 ml volume with ddH$_2$O. The meclizine-HPBCD solution is sterile filtered through 0.22 μm filters and filled aseptically into 1 ml vials. The meclizine content and stability was determined and monitored by HPLC on a monthly basis. HPLC analysis demonstrated that the meclizine-HPBCD solution was stable at 25° C. and at 40° C. for at least 3 months.

EXAMPLE 7

2000 mg HPBCD is weighed off and dissolved in 25 ml ddH$_2$O at ambient temperature. The volume is brought to 35 ml with de-oxygenated WFI. 20 mg edetate disodium is added to the solution. 200 mg meclizine is added to the HPBCD and edetate disodium solution and is vigorously stirred, during which time essentially all of the meclizine is complexed and goes into solution. The pH is measured to be 2.2 and is adjusted to 3.5 with a 0.5 M NaOH solution. The meclizine-HPBCD solution is made to 40 ml volume with de-oxygenated WFI. The meclizine-HPBCD solution is sterile filtered through 0.22 μm filters and filled aseptically into 1 ml vials. The meclizine content and stability was determined and monitored by HPLC on a monthly basis. HPLC analysis demonstrated that the meclizine-HPBCD solution was stable at 25° C. and at 40° C. for at least 6 months.

EXAMPLE 8

2000 mg HPBCD is weighed off and dissolved in 25 ml ddH$_2$O at ambient temperature. The volume is brought to 35 ml with ddH$_2$O. 200 mg meclizine is added to the HPBCD solution and is vigorously stirred for 60 minutes. The pH is adjusted to pH 3.5 with a 0.5 M NaOH solution. The meclizine-HPBCD solution is made to 40 ml volume with ddH$_2$O. The meclizine-HPBCD solution is sterile filtered through 0.22 μm filters and filled aseptically into 1 ml vials. The vials are freeze-dried to produce a solid meclizine-HPBCD inclusion complex and sealed. The solid meclizine-HPBCD inclusion complex is readily dissolved during reconstitution prior to use. The meclizine content and stability was determined and monitored by HPLC on a monthly basis. The solid meclizine-HPBCD inclusion complex was found to be stable at 25° C. and at 40° C. for at least 6 months.

EXAMPLE 9

8000 mg SBECD is weighed off and dissolved in 30 ml ddH$_2$O at ambient temperature. The volume is brought to 35 ml with ddH$_2$O. 200 mg meclizine is added to the SBECD solution and is vigorously stirred, during which time essentially all of the meclizine is complexed and goes into solution. The pH is adjusted to 4.0 with a 0.5 M NaOH solution. The meclizine-SBECD solution is made to 40 ml volume with ddH$_2$O. The meclizine-SBECD solution is sterile filtered through 0.22 μm filters and filled aseptically into 2 ml injection vials and stoppered. The meclizine content was determined by HPLC.

EXAMPLE 10

A 300 mg/ml HPBCD solution is prepared by dissolving 1500 mg HPBCD in 40 ml 0.5 M acetate buffer (sparged with nitrogen gas) at ambient temperature, after which it is made to 50 ml volume with the 0.5 M acetate buffer. 100 mg meclizine is added to 20 ml of the 300 mg/ml HPBCD solution and is vigorously stirred, during which time essentially all of the meclizine is complexed and goes into solution. The pH is measured to be 4.0 and the meclizine-HPBCD solution is sterile filtered through 0.22 μm filters and filled aseptically into 2 ml injection vials and stoppered. The meclizine content and stability was determined and monitored by HPLC on a monthly basis. HPLC analysis demonstrated that the 5 mg/ml meclizine-HPBCD solution was stable at 25° C. and at 40° C. for at least 3 months and the pH remained at 4.

EXAMPLE 11

A 300 mg/ml HPBCD solution is prepared by dissolving 1500 mg HPBCD in 40 ml 0.5 M acetate buffer (sparged with nitrogen gas) at ambient temperature, after which it is made to 50 ml volume with the 0.5 M acetate buffer. 500 mg meclizine is added to 20 ml of the 300 mg/ml HPBCD solution and is vigorously stirred, during which time essentially all of the meclizine is complexed and goes into solution. The pH is measured to be 4.0 and the meclizine-HPBCD solution is sterile filtered through 0.22 μm filters and filled aseptically into 2 ml injection vials and stoppered. The meclizine content and stability was determined and monitored by HPLC on a monthly basis. HPLC analysis demonstrated that the 25 mg/ml meclizine-HPBCD solution was stable at 25° C. and at 40° C. for at least 3 months and the pH remained at 4.

Thus, we have demonstrated that meclizine forms inclusion complexes with cyclodextrins in solution and that it is possible to produce a stable, substantially clear formulations, the formulations being provided with an aqueous carrier pH of about 2 to about 7, the viable formulations of meclizine being suitable for injection.

We claim:

1. A method of treating a vertigo condition, the method comprising:
    providing a pharmaceutically acceptable formulation consisting essentially of:
        a therapeutically effective amount of meclizine;
        a molar excess of at least one cyclodextrin selected from the group consisting of 2-hydroxypropyl-β-cyclodextrin and sulfobutyl ether-β-cyclodextrin;
        an aqueous carrier medium, the aqueous carrier medium having a pH between about 3 to about 7; and
        optionally a pharmaceutically acceptable preservative, a pharmaceutically acceptable antioxidant, a pharmaceutically acceptable osmolality adjusting agent, or combination thereof; and
    injecting the pharmaceutically acceptable formulation in a subject in need thereof.

2. The method of claim 1, wherein the vertigo condition is benign paroxysmal positional vertigo.

3. The method of claim 1, wherein the molar ratio of meclizine to the cyclodextrin is between about 1:2 to about 1:30.

4. The method of claim 1, wherein the molar ratio of meclizine to the cyclodextrin is about 1:13.

5. The method of claim 1, wherein the cyclodextrin has a degree of substitution between 0.5 to 10.0.

6. The method of claim 1, wherein the pharmaceutical formulation remains stable at least three months at 40 degrees centigrade, as determined by high-performance liquid chromatography (HPLC).

7. The method of claim 1, wherein the cyclodextrin is 2-hydroxypropyl-β-cyclodextrin.

8. The method of claim 1, wherein the injecting is subcutaneously.

9. The method of claim 1, wherein the injecting is intramuscularly.

10. The method of claim 1, wherein the injecting is intravenously.

11. The method of claim 1, wherein the injecting is intradermally.

12. The method of claim 1, wherein the therapeutically effective amount of meclizine is between about 2.5 mg/mL to about 5.0 mg/mL.

13. The method of claim 1, wherein the between about 2.5 mg/mL to about 5.0 mg/mL of meclizine is injected subcutaneously.

14. The method of claim 1, wherein the between about 2.5 mg/mL to about 5.0 mg/mL of meclizine is injected intramuscularly.

15. The method of claim 1, wherein the between about 2.5 mg/mL to about 5.0 mg/mL of meclizine is injected intravenously.

16. The method of claim 1, wherein the between about 2.5 mg/mL to about 5.0 mg/mL of meclizine is injected intradermally.

17. A method of treating or preventing a nausea or vomiting condition, the method comprising:
    providing a pharmaceutically acceptable formulation consisting essentially of:

a therapeutically effective amount of meclizine;

a molar excess of at least one cyclodextrin selected from the group consisting of 2-hydroxypropyl-β-cyclodextrin and sulfobutyl ether-β-cyclodextrin;

an aqueous carrier medium, the aqueous carrier medium having a pH between about 3 to about 7; and optionally a pharmaceutically acceptable preservative, a pharmaceutically acceptable antioxidant, a pharmaceutically acceptable osmolality adjusting agent, or combination thereof; and injecting the pharmaceutically acceptable formulation in a subject in need thereof.

18. The method of claim 17, wherein the subject is administered the therapeutically effective amount of meclizine pre-, peri-, or post-operatively.

19. The method of claim 17, wherein the subject is administered the therapeutically effective amount of meclizine pre-, peri-, or post-chemotherapy treatment.

20. The method of claim 17, wherein the molar ratio of meclizine to the cyclodextrin is between about 1:2 to about 1:30.

21. The method of claim 17, wherein the molar ratio of meclizine to the cyclodextrin is about 1:13.

22. The method of claim 17, wherein the cyclodextrin has a degree of substitution between about 0.5 to about 10.0.

23. The method of claim 17, wherein the pharmaceutical formulation remains stable at least three months at 40 degrees centigrade, as determined by high-performance liquid chromatography (HPLC).

24. The method of claim 17, wherein the cyclodextrin is 2-hydroxypropyl-β-cyclodextrin.

25. The method of claim 17, wherein the injecting is subcutaneously.

26. The method of claim 17, wherein the injecting is intramuscularly.

27. The method of claim 17, wherein the injecting is intravenously.

28. The method of claim 17, wherein the injecting is intradermally.

29. The method of claim 17, wherein the therapeutically effective amount of meclizine is between about 2.5 mg/mL to about 5.0 mg/mL.

30. The method of claim 17, wherein the between about 2.5 mg/mL to about 5.0 mg/mL of meclizine is injected subcutaneously.

31. The method of claim 17, wherein the between about 2.5 mg/mL to about 5.0 mg/mL of meclizine is injected intramuscularly.

32. The method of claim 17, wherein the between about 2.5 mg/mL to about 5.0 mg/mL of meclizine is injected intravenously.

33. The method of claim 17, wherein the between about 2.5 mg/mL to about 5.0 mg/mL of meclizine is injected intradermally.

* * * * *